United States Patent [19]

Bloom et al.

[11] 4,134,888

[45] Jan. 16, 1979

[54] CHOLESTERYL CARBONATES AND CARBAMATES OF AZO DYES

[75] Inventors: Allen Bloom, East Windsor; Ling K. Hung, Edison, both of N.J.

[73] Assignee: RCA Corporation, New York, N.Y.

[21] Appl. No.: 772,997

[22] Filed: Feb. 28, 1977

Related U.S. Application Data

[62] Division of Ser. No. 642,728, Dec. 22, 1975, Pat. No. 4,032,470.

[51] Int. Cl.² .................... C07C 107/06; C09B 43/18
[52] U.S. Cl. ............................... 260/207.1; 260/207
[58] Field of Search .................. 260/207, 207.1, 205, 260/206; 252/299; 350/160 LC

[56] References Cited

U.S. PATENT DOCUMENTS

| | | | |
|---|---|---|---|
| 3,720,658 | 3/1973 | Goldberg et al. | 260/207.1 |
| 3,984,392 | 10/1976 | van der Veen | 260/206 |
| 4,027,950 | 6/1977 | Moriyama et al. | 252/299 X |

FOREIGN PATENT DOCUMENTS 2024269 12/1971 Fed. Rep. of Germany ........... 260/206

OTHER PUBLICATIONS

Lubs, *The Chemistry of Synthetic Dyes and Pigments*, Reinhold Publishing Corp., New York, 1955, pp. 670–671.

*Primary Examiner*—Charles F. Warren
*Attorney, Agent, or Firm*—H. Christoffersen; Birgit E. Morris

[57] ABSTRACT

Novel liquid crystal dyes of the formula

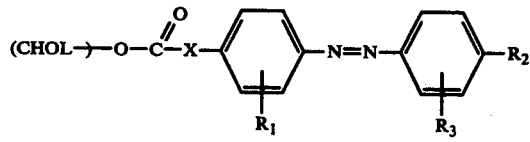

wherein (CHOL—) is a cholesteryl radical, X can be O or NH, $R_1$ can be H, —OH, methyl, fluoro or chloro; $R_2$ can be —$NO_2$, —CN, N-(alkyl)$_2$, —OCOOR, —OCOR, alkyl or alkoxy and $R_3$ can be H, methyl, fluoro or chloro, can be added to known liquid crystal compositions to impart color to the mixtures and improved contrast to a liquid crystal electro-optic device containing such mixtures.

2 Claims, 1 Drawing Figure

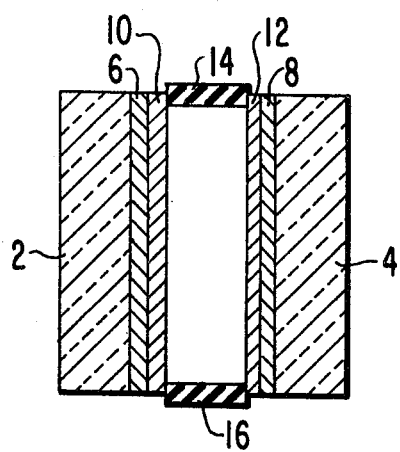

CHOLESTERYL CARBONATES AND CARBAMATES OF AZO DYES

This is a division of application Ser. No. 642,728, filed Dec. 22, 1975, now U.S. Pat. No. 4,032,470.

This invention relates to novel liquid crystal devices. More particularly, this invention relates to liquid crystal mixtures and devices containing novel liquid crystalline dyes.

BACKGROUND OF THE INVENTION

Electro-optic devices containing liquid crystal materials have become commercially important recently because of their low power requirements and good contrast, particularly for applications such as watch faces, calculator displays and the like. Although liquid crystal compounds have been known for many years, the discovery of nematic liquid crystals that have a transition temperature range that spans room temperature sparked a renewed interest in these materials and greatly expanded their marketability. Research is continuing to discover new room temperature liquid crystal materials and mixtures and for liquid crystal materials having improved contrast in electro-optic devices.

SUMMARY OF THE INVENTION

We have discovered novel liquid crystal dye compounds, substituted cholesteryl p-phenylazophenyl carbonates and carbamates. These liquid crystals, when admixed in small amounts with low melting liquid crystal materials, impart strong colors to the mixtures but without materially affecting the transition temperature range of the liquid crystal composition to which they are added. The present dyes thus improve the color contrast of electro-optic devices employing these liquid crystal materials, and impart decorative colors in the yellow to orange to red hues, without adversely affecting other properties of the liquid crystals.

BRIEF DESCRIPTION OF THE DRAWING

The FIGURE is a cross-sectional view of an electro-optic device embodying the invention.

DETAILED DESCRIPTION OF THE INVENTION

The novel liquid crystal dyes of the present invention have the formula

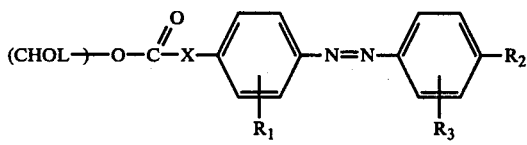

wherein (CHOL)— represents a cholesteryl radical, X can be O or NH, $R_1$ can be hydrogen, hydroxy, methyl, fluoro or chloro; $R_2$ can be —$NO_2$, —CN, —N(alkyl)$_2$, —OCOOR, —OCOR, alkyl or alkoxy and $R_3$ can be hydrogen, methyl, fluoro or chloro. The length of the $R_2$ alkyl group is not critical, although lower molecular weight groups of 1 to about 20 carbon atoms are more readily available.

These dyes are comparatively high melting, deeply colored materials and as such are of little interest alone in liquid crystal cells. However, these compounds, and the compound wherein in the above formula $R_1$ and $R_3$ are hydrogen and $R_2$ is also hydrogen, which is a known compound disclosed by Schadendorff and Verdino, published in Monatsh, Vol. 65, pages 338–47 (1935), see also U.S. Pat. No. 3,720,658 to Goldberg et al, can be admixed with low melting liquid crystal compounds in small amounts to impart strong colors to the mixtures but without materially changing their use temperature range.

The above-described liquid crystalline dyes can be prepared by reacting equimolar amounts of cholesteryl chloroformate and the appropriate p-hydroxyazodiphenyl or p-aminodiphenyl compound in a solvent. The product is isolated and purified in known manner, as by recrystallization.

The dyes can be admixed with nematic liquid crystal compositions to impart a color characteristic of each dye. Low melting nematic liquid crystal compositions, particularly p-alkoxybenzylidene-p'-alkylanilines and their mixtures with other liquid crystals, and mixtures of p-alkoxy- or -acyloxybenzylidene-p'-cyanoanilines, have a transition temperature range that includes room temperature, are particularly suitable. The exact amount of dye to be added depends on the solubility of the dye in the liquid crystal composition and also on the color desired. In general, from about 0.05% up to about 2% by weight of the liquid crystal mixture of the dyestuff will be employed.

P-alkoxybenzylidene-p'-butylanilines are known liquid crystals and are described for example in U.S. Pat. No. 3,829,491 which issued Aug. 13, 1974 to Strebel. Mixtures of p-methoxybenzylidene-p'-n-butylaniline (hereinafter referred to as MBBA) and p-ethoxybenzylidene-p'-n-butylaniline (hereinafter referred to as EBBA) have particularly broad and low use temperature ranges. Mixtures containing about 35 to about 70% by weight of MBBA are preferred.

P-alkoxybenzylidene-p'-cyanoanilines are also known and are described in U.S. Pat. No. 3,499,702, issued Mar. 10, 1970, to Goldmacher et al. P-acyloxybenzylidene-p'-cyanoanilines have been disclosed by Castellano in U.S. Pat. No. 3,597,044.

In preparing an electro-optic device, the liquid crystal compounds should be rigorously purified to remove ionic and nonionic impurities which may react to degrade the liquid crystal compounds either by decomposition, transubstitution reactions and the like. For commercially acceptable cells, the liquid crystal compounds should be purified so that their resistivity is $1 \times 10^{11}$ ohm-cm or higher.

After the liquid crystal compounds are mixed together, a small amount of a chiral aligning agent is advantageously added. The aligning agent serves to orient the molecules of the mixture in the same direction since chiral compounds normally twist in a right-handed or left-handed direction. Suitable aligning agents include cholesteryl derivatives, such as cholesteryl halides, cholesteryl esters and the like; optically active compounds such as d- or l-α-pinene, d- or l-octanol and chiral esters such as 4-propylphenyl-4'-(4''-2-methylbutylphenylcarboxy)-2-chlorobenzoate having the formula

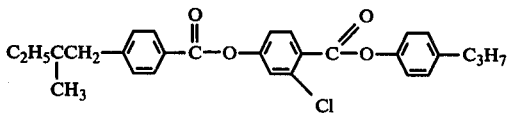

and the like. The amount of the chiral aligning agent added is not critical, but in general from about 0.05 to about 2.0% by weight of the liquid crystal composition is suitable.

Referring to the Figure, a liquid crystal cell is constructed from two glass plates 2 and 4 having conductive indium-doped tin oxide coatings 6 and 8, respectively on facing surfaces thereof. Thin silicon oxide layers 10 and 12 are evaporated onto the conductive layers 6 and 8, respectively, at an angle of 60 degrees. One-half mil (25.4 microns) thick glass frit spacers 14 and 16 maintain the coated glass plates 2 and 4 apart to complete the cell components. The cell is baked at 525° C. to melt the glass frit and seal the cell except for a fill port. The cell is filled with the desired liquid crystal composition in the isotropic state and hermetically sealed with solder.

The invention will be further illustrated by the following Examples but it is to be understood that the invention is not meant to be limited to the details disclosed therein. In the Examples, parts and percentages are by weight unless otherwise noted.

EXAMPLE 1

A round bottom flask equipped with a magnetic stirrer and a reflux condenser was charged with 10 millimols of 4-hydroxy-4'-nitrophenylazobenzene, an equimolar amount of cholesteryl chloroformate and 125 milliliters of benzene. The mixture was heated in an oil bath until a homogeneous solution formed, when 2 milliliters of pyridine was added. The mixture was refluxed for 18 hours and cooled to form a gelatinous mass. The product mixture was heated and filtered through a silicic acid bed deposited on a glass fritted Buchner funnel. The product on the filter funnel was purified by washing with chloroform and removing the solvent under vacuum. The purification was repeated until only one product remained on the filter, as shown by a thin layer chromatogram. The product was then recrystallized from a chloroform/methyl ethyl ketone solution to a constant methyl point range.

Cholesteryl 4-azophenyl (4'-nitrobenzyl) carbonate was obtained in 23.3% yield. This compound has the formula

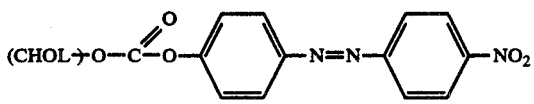

wherein (CHOL)— has the meaning given above. This compound has an orange-red color and a liquid crystal temperature range of 219–256° C. The structure was confirmed by elemental, infrared and nuclear magnetic resonance analyses. Spectrophotometric measurements were also made. The absorption maximum in the visible region in chloroform solution was 340 nanometers. The maximum molar extinction coefficient in chloroform solution was 28,400 liter (molcentimeter)$^{-1}$.

EXAMPLES 2–5

Additional liquid crystal dye compounds were prepared following the procedure of Example 1 except substituting the appropriate hydroxyazobenzene or aminoazobenzene compound. The reaction solvent for the compound of Example 5 was toluene containing 1% by volume of pyridine. The structures and properties are summarized in Table I below:

Table I

| Ex. | Compound | Yield % | Liquid Crystal Temp. Range, ° C. | Color | Maximum Wavelength nm | Molar Extinction Coefficient, liter (mol-cm)$^{-1}$ |
|---|---|---|---|---|---|---|
| 2 | cholesteryl 4-azophenyl-(4'-cyanophenyl) carbonate (CHOL)−O−C(=O)−O−⟨⟩−N=N−⟨⟩−CN | 83.4 | 226–250 | orange | 332 | 29,600 |
| 3 | cholesteryl 4-phenylazophenyl carbonate (CHOL)−O−C(=O)−O−⟨⟩−N=N−⟨⟩ | 85 | 169–214 | yellow-orange | 322 | 24,400 |
| 4 | cholesteryl 4-(3-hydroxy)azophenyl-(4'-nitrophenyl)carbonate (CHOL)−O−C(=O)−O−⟨⟩−N=N−⟨OH⟩−NO$_2$ | 59.5 | 213–243 | red | 343 | 20,200 |
| 5 | cholesteryl 4-azophenyl-(4'-diethyl aminophenyl) carbamate (CHOL)−O−C(=O)−NH−⟨⟩−N=N−⟨⟩−N−(CH$_2$CH$_3$)$_2$ | 58 | 137–215 | orange-red | 430[a] | 37,330[a] |

[a] in dimethylformamide solution

EXAMPLE 6

The liquid crystal dyes prepared in Examples 2–4 were admixed with MBBA and the nematic to isotropic liquid transition temperature (NL) range measured. The results are summarized below in Table II.

Table II

| Dye of Example | Weight % of Dye | NL, °C |
| --- | --- | --- |
| 2 | 0.154 | 44.0-44.8 |
| 3 | 0.618 | 42.9-43.9 |
| 4 | 0.489 | 42.9-44.5 |
| Control (MBBA) | — | 44.4-44.8 |

EXAMPLE 7

The liquid crystal dyes prepared in Examples 2-5 were admixed with an equimolar mixture of MBBA and EBBA and the nematic to isotropic liquid transition temperature range measured. The results are summarized below in Table III.

Table III

| Dye of Example | Weight % of Dye | NL, °C. |
| --- | --- | --- |
| 2 | 0.212 | 60.5-61.4 |
| 3 | 0.247 | 60.7-61.3 |
| 4 | 0.128 | 60.2-60.9 |
| 5 | 1.129 | 61.1-61.7 |
| Control | — | 61.0-61.4 |

EXAMPLE 8

The liquid crystal dye prepared in Example 1 was admixed (0.066%) with an equimolar mixture of 4-n-butoxybenzylidene-4'-aminobenzonitrile, 4-n-hexoxybenzylidene-4'-aminobenzonitrile and 4-n-octanoyloxybenzylidene-4'-aminobenzonitrile. The resultant mixture had a yellow to orange color and an NL temperature range of 86-90° C.

EXAMPLE 9

A mixture of 0.21% of the liquid crystal dye of Example 5 and a 70:30 mol ratio of MBBA and EBBA containing 15% of 4-ethoxybenzylidene-4'-aminobenzonitrile was charged to a liquid crystal cell as in the Figure. The liquid crystal mixture was aligned parallel to the face of the cell. The optical density, as seen through plane polarized light parallel to the liquid crystal orientation, was measured at the visible absorption maximum (420 nm) as a function of applied voltage. The results which show that as the voltage is increased the color fades, are summarized in Table IV below:

Table IV

| Voltage | Optical Density |
| --- | --- |
| 0 | 0.717 |
| 1 | 0.717 |
| 2 | 0.675 |
| 4 | 0.484 |
| 6 | 0.449 |
| 8 | 0.418 |
| 10 | 0.410 |
| 15 | 0.390 |
| 20 | 0.386 |

We claim:
1. A compound of the formula

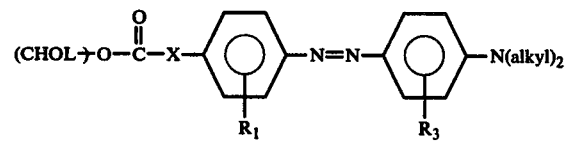

wherein (CHOL)— represents a cholesteryl radical, X can be O or NH, $R_1$ can be hydrogen, hydroxy, methyl, fluoro or chloro; and $R_3$ can be hydrogen, methyl, fluoro or chloro.

2. A compound according to claim 1 wherein said compound is cholesteryl 4-azophenyl-(4'-diethylaminophenyl)carbamate.